US00PP26913P3

(12) United States Plant Patent
McElrea

(10) Patent No.: US PP26,913 P3
(45) Date of Patent: Jul. 5, 2016

(54) ***AGAPANTHUS* HYBRID PLANT NAMED 'LMAGGIE1'**

(50) Latin Name: ***Agapanthus* hybrid**
Varietal Denomination: LMAggie1

(71) Applicant: Laurence E. McElrea, Perris, CA (US)

(72) Inventor: Laurence E. McElrea, Perris, CA (US)

( * ) Notice: Subject to any disclaimer, the term of this patent is extended or adjusted under 35 U.S.C. 154(b) by 38 days.

(21) Appl. No.: 14/120,512

(22) Filed: May 28, 2014

(65) Prior Publication Data

US 2015/0351305 P1 Dec. 3, 2015

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Susan McCormick Ewoldt
(74) *Attorney, Agent, or Firm* — Samuel R McCoy, Jr.

(57) ABSTRACT

'LMAggie1' is a distinctive *Agapanthus* hybrid seedling selection, which is characterized by evergreen foliage, a short plant height, a short inflorescence height and dark purple flowers.

2 Drawing Sheets

Latin name of the genus and species: The Latin name of the novel variety disclosed herein is *Agapanthus* hybrid 'LMAggie1'.

Variety denomination: The inventive variety of *Agapanthus* hybrid disclosed herein has been given the variety denomination 'LMAggie1'.

BACKGROUND OF THE INVENTION

The present invention relates to a new and distinct variety of *Agapanthus* hybrid, which has been named 'LMAggie1'. Its market class is that of an ornamental flowering perennial. *Agapanthus*, commonly called "lily of the Nile", is a flowering perennial native to South Africa that forms clumps of dark green strap-like leaves. In summer, umbels rise above the foliage which bear numerous flowers in colors ranging from pale violet to dark purple. Its consistent size and performance, combined with its attractive inflorescences through its hardiness range make it an ideal choice for specimen, borders and mass plantings in any full to filtered sun to shady, low-maintenance landscape or container.

Parentage: The cultivar 'LMAggie1' is a seedling selection resulting from the controlled pollination of seed parent *Agapanthus praecox* subsp. *minimus* (unnamed and unpatented) and pollen parent *Agapanthus* hybrid 'Mood Indigo' (unpatented) performed at a residence in Lake Mathews, Calif. in 2004. Said seedling was first observed in 2005 and was noted as exhibiting evergreen foliage, a short plant height, and a short inflorescence height like that of the seed parent, but possessing dark purple flowers like those of the pollen parent. Said seedling was isolated for further observation and was subsequently grown and asexually propagated through many generations from 2005 until 2014, at which time it was determined that the characteristics for which it was originally selected were uniform and stable. The new plant was given the name 'LMAggie1'.

Asexual Reproduction: 'LMAggie1' was first asexually propagated by dividing the root-bearing, rhizomatous propagules of the plant (i.e. "division cloning") in 2005 in Lake Matthews, Calif. and has since been asexually propagated through nine subsequent generations. The distinctive characteristics of the inventive 'LMAggie1' variety are stable from generation to generation; clones of the variety produced by asexual reproduction maintain the distinguishing characteristics of the original plant.

SUMMARY OF THE INVENTION

'LMAggie1' is a distinctive *Agapanthus* hybrid seedling selection, which is characterized by evergreen foliage, a short plant height, a short inflorescence height and dark purple flowers.

DETAILED BOTANICAL DESCRIPTION OF THE VARIETY

Figure 1:
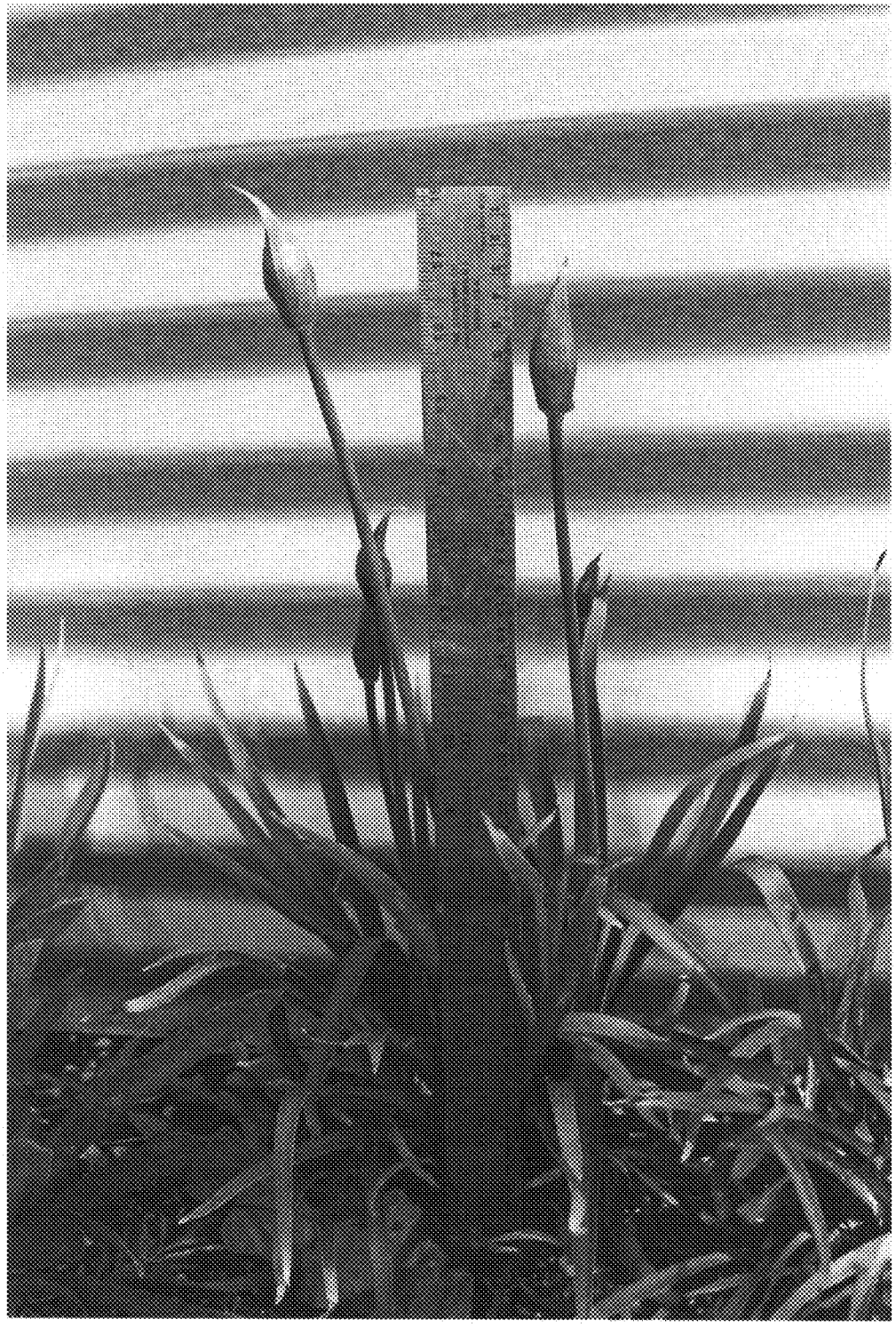
FIG. 1 shows an exemplary 'LMAggie1' specimen, approximately 12 months of age, grown in ground.
Figure 2:
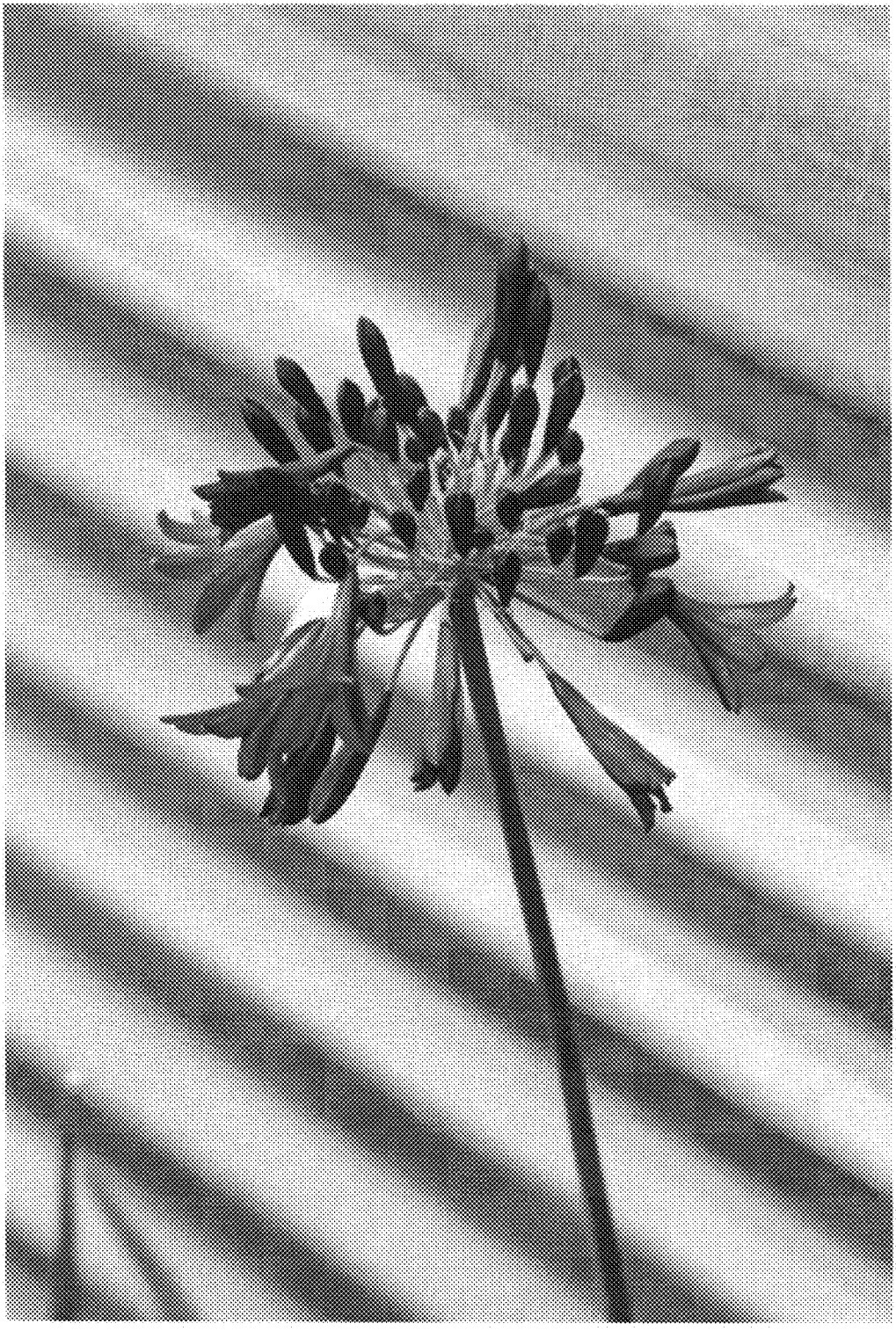
FIG. 2 shows an exemplary umbel of 'LMAggie1'.

The following is a detailed botanical description of a new and distinct *Agapanthus* hybrid seedling selection known as 'LMAggie1'. Unless indicated otherwise, the descriptions disclosed herein are based upon observations made in May 2014 of mature 'LMAggie1' plants, approximately 12 months of age, grown in-ground at a residence in Perris, Calif. Plants were grown in full sun; fertilized with slow release granular fertilizer and regularly watered with overhead irrigation. No pest or disease measures were taken during production.

Those skilled in the art will appreciate that certain characteristics will vary with older or, conversely, with younger plants. 'LMAggie1' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1986 edition. Note that generic color descriptions such as "green" do not exist in the R.H.S. charts and the corresponding R.H.S. colors are quoted.

The distinguishing features and other characteristics of *Agapanthus* hybrid 'LMAggie1' are apparent from the description provided below.

Growth Habit, Dimensions and Color

Plant description:

*Plant habit*.—Rhizomatous herbaceous perennial with an arching habit.

*Height*.—22 cm to the tallest leaf with the majority of foliage at or below 20 cm, as measured.

*Width*.—35 cm, as measured.

*Bloom period*.—Spring.

*Hardiness*.—USDA Zone 9 to 10.

*Environmental tolerances*.—Prefers to be grown in full sun. Drought tolerant once established; moderate to good recovery with watering after severe wilting. Tolerates a wide range of soil types from sandy loam to loamy clay.

*Pest and disease susceptibility or resistance*.—In common with the species, none of note.

*Propagation*.—Propagation is accomplished through division of rhizomes.

*Time to initiate roots*.—Approximately 3 weeks.

*Crop time*.—Depending on latitude of and microclimate of growing location, a fully rooted cutting requires approximately 3 months with an additional 5 to 7 months needed to produce a mature and marketable 15 cm container.

Roots: The roots are fibrous and freely-branched, colored white, fleshy, similar to other *Agapanthus*; high root density.

Stem:

*Branching habit*.—Acaulescent, rhizomatous plant with shoots emerging from rhizomes with an upright attitude.

Basal shoots:

*Shoots density*.—7 divisions, or propagules, per one square foot area, with the oldest propagules near the center of the plant's crown possessing 10 to 12 leaves and shoots of varying ages and sizes.

*Shoot strength*.—Medium.

*Cross section*.—Concave.

*Shoot color* (*adaxial & abaxial surfaces*).—Green (RHS 143C).

*Anthocyanin intonations*.—None.

*Shoot surface texture*.—Smooth.

Foliage:

*Type*.—Evergreen.

*Arrangement*.—Basal.

*Division*.—Simple.

*Attitude*.—Arched.

*Shape*.—Linear.

*Apex*.—Acute.

*Base*.—Sheathed.

*Cross section*.—Flat.

*Venation*.—Parallel.

*Vein color* (*adaxial surfaces*).—Same as surrounding foliage.

*Vein color* (*abaxial surfaces*).—Same as surrounding foliage.

*Margins*.—Entire.

*Attachment*.—Acaulescent.

*Texture*.—Smooth and glossy.

*Surface hairiness* (*adaxial surface*).—Glabrous.

*Surfaces hairiness* (*abaxial surface*).—Glabrous.

*Mature leaf dimensions*.—Longest observed leaf measuring length 320 mm, average width 15.5 mm at widest point.

*Mature leaf color* (*adaxial & abaxial surface*).—Yellow green (RHS 146B).

*Anthocyanin intonations*.—None.

*Petiole*.—Leaves are acaulescent; sessile.

*Stipules*.—Absent.

Inflorescence:

*Inflorescence type*.—Umbellate.

*Inflorescence shape, lateral view*.—Narrow oblate.

*Umbel diameter*.—Largest observed is 11 cm wide.

*Number of umbels per pot*.—Potentially one inflorescence per division.

*Number of flowers per umbel*.—Ranging from 30 to 45 flowers.

*Scape dimensions*.—Largest observed measuring at 40 cm tall and 6 mm wide at the base.

*Bract*.—Shape, lateral view — Ovate. Apex — Short, acuminate. Dimensions — Approximately 60 mm long and 25 mm wide. Color — A combination or yellow-green (RHS 144A) and greyed-purple (RHS 183D); general tonality is greyed-purple RHS 183D. Texture — Smooth.

*Other characteristics of scape*.—Color is yellow green (RHS 144A); cylindrical shape; texture is smooth; glabrous.

Buds:

*Bud shape*.—Obelliptic; apex round; base cuneate.

*Bud dimensions*.—35 mm long and 7 mm wide, prior to anthesis.

*Bud color*.—Appearing as a combination of purple 79A (RHS 79A), purple (RHS 79B) and violet (RHS 83A).

*Bud texture*.—Glabrous.

Flowers:

*General*.—Apetalous flowers; shape is campanulate; self-cleaning and non-fragrant. Attitude is upward and outward. Bloom period is spring and summer.

*Beginning of flowering*.—Medium.

*Pedicel dimensions*.—16 mm long and 1.5 mm wide, as measured.

*Pedicel color*.—A combination of yellow green (RHS 144A) and purple (RHS 79A).

*Pedicel surface*.—Glabrous.

*Perianth dimensions*.—Approximately 28 mm wide and 35 mm long, at anthesis.

*Tepals*.—Six basally fused tepals.

*Tepal shape*.—Oblanceolate; apex is round.

*Tepal dimensions*.—37 mm long and 7 mm wide, as measured.

*Outer tepal color*.—Purple (RHS 79B), yet appearing as violet (RHS 86A) under high light exposure.

*Inner tepal color*.—Purple (RHS 79B) at both the midrib and the margins with purple (RHS 76D) in areas between margins and midrib.

*Tepal surface*.—Smooth; glabrous.

*Tepal margin*.—Entire.

Reproductive organs:

*Stamens*.—Six.

*Stamen attachment*.—Each is adnate to a corresponding tepal.

*Filament color*.—Purple (RHS 76C) at base, becoming Purple (RHS 76B) near apex.

*Filament dimensions*.—23 mm long and less than 1 mm wide.

*Anther attachment*.—Versatile.

*Anther dimensions*.—4 mm long and 1.5 mm wide.

*Anther color*.—Appearing as a mixture of black (RHS 202A) and purple (RHS 79A).

*Pollen*.—Present; high quantity; color appears to be a mixture of black (RHS 202A) and purple (RHS 79A).

*Staminodes*.—Absent.

*Pistil*.—One.

*Pistil dimensions*.—14 mm long, from apex of ovary; width is approximately 1 mm.

*Pistil color*.—Purple (RHS 76C) at base, becoming Purple (RHS 76B) near apex.

*Ovary shape*.—Oblong.

*Ovary color*.—Yellow-green (RHS 150B).

*Ovary dimensions*.—10 mm long and 2.5 mm wide.

*Ovary position*.—Superior.

*Pistillodes*.—Absent.

Fruit and seeds: Not observed.

Comparisons with other *Agapanthus*.

'LMAggie1' is most similar to the seed parent, *Agapanthus praecox* subsp. *minimus*, in that both are characterized by evergreen foliage, similar overall plant height, similar inflorescence height and similar flower count. However, there are several characteristics that distinguish 'LMAggie1' from the seed parent. The flowers of 'LMAggie1' are dark purple (RHS 79B) whereas the flowers of the seed parent are described as a pale violet blue, approximated to violet blue (RHS 92C) on the outer perianth. The flower count of 'LMAggie1' ranges from 30 to 45 flowers whereas the flower count of the seed parent is lower, ranging from 20 to 30 flowers. The leaves of 'LMAggie1' are 15.5 mm wide whereas the leaves of the seed parent are 12.5 mm wide. The leaf cross section of 'LMAggie1' is flat whereas the seed parent is slightly folded adaxially at the midrib. The plant habit of 'LMAggie1' is arching whereas the habit of the seed parent is weeping.

'LMAggie1' is similar to the pollen parent, *Agapanthus* hybrid 'Mood Indigo', in that both have dark purple flowers and a similar number of flowers per umbel. However there are characteristics that distinguish 'LMAggie1' from 'Mood Indigo'. 'LMAggie1' is an evergreen perennial whereas 'Mood Indigo' is deciduous. The flower attitude of 'LMAggie1' is upward and outward whereas the flowers of 'Mood Indigo' are pendulous.

With respect to commercial varieties, there are no varieties known to the breeder that exhibit the combination of dark purple flowers, short foliage height and short inflorescence height of 'LMAggie1'. There are several *Agapanthus* cultivars that are described to have dark violet flowers like those of 'LMAggie1' however each of these varieties exhibit inflorescences that are taller than that of 'LMAggie1': *Agapanthus* 'Northern Star' (U.S. Plant Pat. No. 20,957), is reported to exhibit foliage height of 60 cm and a scape length of 100 cm; *Agapanthus* 'Senna' (U.S. Plant Pat. No. 19,972) is reported to exhibit foliage dimensions of 30 cm tall and over 40 cm wide with an overall height, in flower, of 96 cm; and, *Agapanthus* 'Elaine' (U.S. Plant Pat. No. 7,303) is described to exhibit an overall height, in flower, of 130 cm.

That which is claimed is:

1. A new and distinct *Agapanthus* hybrid plant selection named 'LMAggie1', substantially as described and illustrated herein.

* * * * *